US 11,439,986 B2

(12) United States Patent
Beletskiy

(10) Patent No.: US 11,439,986 B2
(45) Date of Patent: Sep. 13, 2022

(54) SILVER IMPREGNATION SOLUTION CONTAINING HIGH-BOILING OXYGENATED ADDITIVE AND ITS USE IN ETHYLENE OXIDE CATALYST PREPARATION

(71) Applicant: Scientific Design Company, Inc., Little Ferry, NJ (US)

(72) Inventor: Evgeny Beletskiy, Teaneck, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 1024 days.

(21) Appl. No.: 15/839,987

(22) Filed: Dec. 13, 2017

(65) Prior Publication Data

US 2019/0176130 A1    Jun. 13, 2019

(51) Int. Cl.
*B01J 23/50* (2006.01)
*C07D 301/02* (2006.01)
(Continued)

(52) U.S. Cl.
CPC ............. *B01J 23/50* (2013.01); *B01J 35/002* (2013.01); *B01J 37/0203* (2013.01);
(Continued)

(58) Field of Classification Search
CPC .. B01J 23/688; B01J 37/0203; B01J 37/0213; B01J 37/06; B01J 23/50; B01J 31/00; B01J 37/0207; B01J 35/1009
(Continued)

(56) References Cited

U.S. PATENT DOCUMENTS 3,563,913 A   2/1971  de Krijger et al.
4,066,575 A   1/1978  Winnick
(Continued)

FOREIGN PATENT DOCUMENTS

CN   104860812 B    7/2017
EP   0724479 B1     6/2001
JP   2004161632 A *  6/2004

OTHER PUBLICATIONS

Machine translation of JP2004161632A (Year: 2004).*
International Search Report and Written Opinion dated Apr. 19, 2019 issued in PCT/US2018/065115.

*Primary Examiner* — Colin W. Slifka
(74) *Attorney, Agent, or Firm* — Scully Scott Murphy and Presser

(57) ABSTRACT

A silver impregnation solution containing: (i) silver ions, (ii) a polar organic additive containing two to four carbon atoms and two to four functional groups selected from hydroxy, carboxylic acid, and amine groups, provided that a carboxylic acid group can only be present along with a hydroxy or amine group, and provided that an amine group can only be present along with a hydroxy or carboxylic acid group; and (iii) water; wherein components (i) and (ii) are water soluble and dissolved in the impregnation solution. Also described herein is a method for producing a catalyst effective in the oxidative conversion of ethylene to ethylene oxide, the method comprising subjecting a refractory carrier impregnated with the above-described silver impregnation solution to a calcination process. Also described herein is a method for converting ethylene to ethylene oxide by use of the foregoing silver catalyst, as produced by the above-described silver impregnation solution.

33 Claims, 7 Drawing Sheets

(51) Int. Cl.
 *B01J 37/02* (2006.01)
 *B01J 35/00* (2006.01)
 *B01J 37/08* (2006.01)
(52) U.S. Cl.
 CPC ............ *B01J 37/0213* (2013.01); *B01J 37/08* (2013.01); *C07D 301/02* (2013.01)
(58) Field of Classification Search
 USPC ....... 502/439, 341, 202, 208, 214, 224, 231, 502/332, 216, 347, 222, 213, 328, 340, 502/207, 229, 348, 226
 See application file for complete search history.

(56) References Cited

U.S. PATENT DOCUMENTS

| | | | |
|---|---|---|---|
| 4,305,844 A | 12/1981 | Vangermain et al. |
| 4,645,754 A | 2/1987 | Tamura et al. |
| 4,761,394 A | 8/1988 | Lauritzen |
| 4,766,105 A | 8/1988 | Lauritzen |
| 4,769,358 A | 9/1988 | Kishimoto et al. |
| 4,908,343 A | 3/1990 | Bhasin |
| 5,011,807 A | 4/1991 | Hayden et al. |
| 5,057,481 A | 10/1991 | Bhasin |
| 5,077,256 A | 12/1991 | Yamamoto et al. |
| 5,099,041 A | 3/1992 | Hayden et al. |
| 5,102,848 A | 4/1992 | Soo et al. |
| 5,112,795 A | 5/1992 | Minahan et al. |
| 5,187,140 A | 2/1993 | Thorsteinson et al. |
| 5,407,888 A | 4/1995 | Herzog et al. |
| 7,102,022 B2 | 9/2006 | Evans et al. |
| 8,546,297 B2 | 10/2013 | Rokicki et al. |
| 8,791,280 B2 | 7/2014 | Rizkalla |
| 8,883,675 B2 | 11/2014 | Rizkalla et al. |
| 9,115,104 B2 | 8/2015 | Guckel |
| 9,345,774 B2 | 5/2016 | Petersson et al. |
| 2005/0027133 A1 | 2/2005 | Hooks et al. |
| 2007/0037991 A1 | 2/2007 | Rizkalla |
| 2010/0140098 A1* | 6/2010 | Uzoh ...................... C25D 3/54 205/96 |
| 2012/0214293 A1* | 8/2012 | Aksu ...................... C25D 7/126 438/478 |
| 2015/0174554 A1* | 6/2015 | Cao ...................... B01J 37/0203 502/348 |

\* cited by examiner (5A)

(5B)

(5C)

(5D)

SILVER IMPREGNATION SOLUTION CONTAINING HIGH-BOILING OXYGENATED ADDITIVE AND ITS USE IN ETHYLENE OXIDE CATALYST PREPARATION

FIELD OF THE INVENTION

The present disclosure relates to silver-based ethylene oxide catalysts for the oxidative conversion of ethylene to ethylene oxide, and in particular, to their preparation. More particularly, the present disclosure relates to silver impregnating solutions containing a high-boiling oxygenated additive (e.g., glycerol or glycolic acid), and their use in producing silver-based ethylene oxide catalysts having high selectivities and/or activities, at least in the start-up phase of ethylene oxide production.

BACKGROUND

As known in the art, high selectivity catalysts (HSCs) for the epoxidation of ethylene refer to those catalysts that possess selectivity values higher than high activity catalysts (HACs) used for the same purpose. Both types of catalysts include silver as the active catalytic component on a refractory support (i.e., "carrier", such as alumina). Typically, one or more promoters are included in the catalyst to improve or adjust properties of the catalyst, such as selectivity. Generally, HSCs achieve the higher selectivity (typically, in excess of 87 mole % or above) by incorporation of rhenium as a promoter. Typically, one or more additional promoters selected from alkali metals (e.g., cesium), alkaline earth metals, transition metals (e.g., tungsten compounds), and main group metals (e.g., sulfur and/or halide compounds) are also included.

There are also ethylene epoxidation catalysts that may not possess the selectivity values typically associated with HSCs, though the selectivity values are improved over HACs. These types of catalysts can also be considered within the class of HSCs, or alternatively, they can be considered to belong to a separate class, e.g., "medium selectivity catalysts" or "MSCs." These types of catalysts may exhibit selectivities of at least 83 mole % and up to 87 mole %. In contrast to HSCs and MSCs, the HACs are ethylene epoxidation catalysts that generally do not include rhenium, and for this reason, do not provide the selectivity values of HSCs or MSCs. Typically, HACs include cesium (Cs) as the only promoter.

It is well known that two of the most important performance criteria for silver catalysts are selectivity and activity of the catalyst, and there is a continuing effort to improve on these characteristics. Of particular importance is the performance of the catalyst over the course of the start-up phase, typically within 150 hours of use in converting ethylene to ethylene oxide under typical industrial conditions. There is also a continuing effort to extend the useful lifetime (i.e., "longevity" or "usable life") of these catalysts by maintaining an effective level of activity and selectivity characteristics over a longer period of time. However, particularly as concerns the start-up phase, there remains a need for further improving the selectivity and activity of these catalysts.

SUMMARY

In one aspect, the present disclosure is directed to a silver impregnating solution (i.e., "liquid silver-containing solution") that includes a polar organic additive containing two to four carbon atoms and two to four functional groups selected from hydroxy, carboxylic acid, and amine groups, provided that a carboxylic acid group can only be present along with a hydroxy or amine group, and provided that an amine group can only be present along with a hydroxy or carboxylic acid group. In particular embodiments, the polar organic additive is selected from ethylene glycol, propylene glycol, glycerol, erythritol, ethane-1,1,2,2-ethanetetrol, glycolic acid, lactic acid, glycine, alanine, and aspartic acid. More specifically, the silver impregnating solution includes the following components: (i) silver ions, (ii) the polar organic additive described above; and (iii) water. Components (i) and (ii) are water soluble and dissolved in the impregnation solution. It has herein been surprisingly found that including the polar organic additive in the silver impregnating solution results in an ethylene oxidation catalyst having a significantly improved performance in selectivity and/or activity, particularly in the start-up phase of an ethylene oxidation process.

In another aspect, the present disclosure is directed to a method for producing a catalyst effective in the oxidative conversion of ethylene to ethylene oxide (i.e., a "silver catalyst"). In the method, a refractory carrier that has been impregnated with the above-described silver impregnation solution is subjected to a calcination process to produce the silver catalyst. Particularly in the start-up phase of an ethylene oxidation reaction, the resulting catalyst has been surprisingly found to exhibit an improved performance in selectivity and/or activity. It has also herein been surprisingly found that exposure of the resulting silver catalyst, as prepared using the above silver impregnating solution, to a high humidity level of at least 80% for at least six hours further increases the selectivity and/or activity benefit of the high-boiling oxygenated additive. Thus, the present disclosure is also directed to a method for converting ethylene to ethylene oxide by use of the above-described silver catalyst, wherein at least the start-up phase of the process has been significantly improved in selectivity and/or activity.

DETAILED DESCRIPTION

Figure 1A:
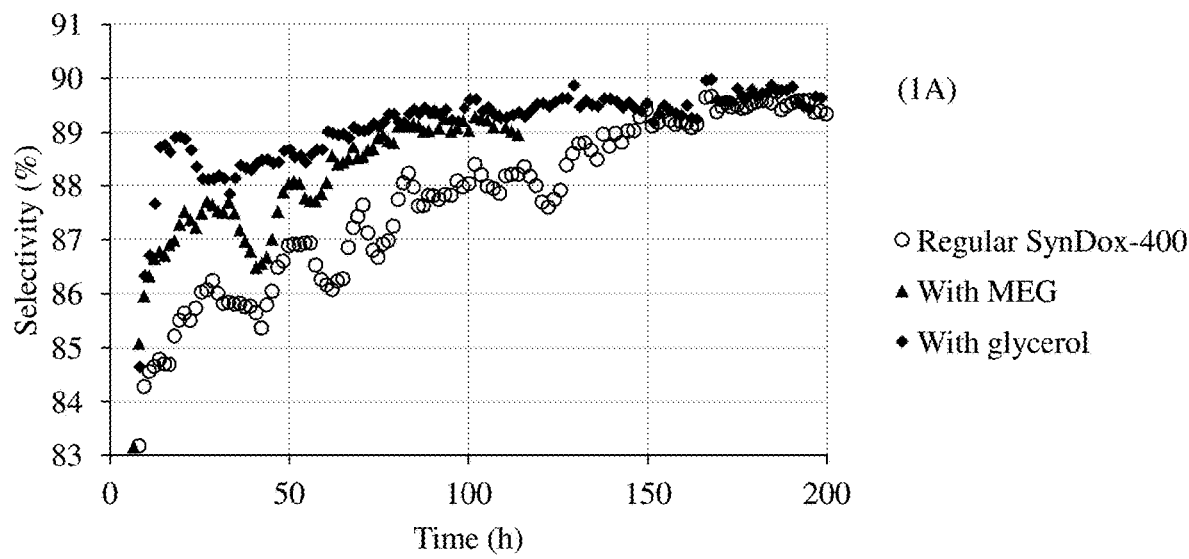
FIGS. 1A and 1B are graphs showing results of microreactor demo testing of SynDox™-400 commercial catalyst and the catalyst modified with 2% MEG- or glycerol-modified formulations.

The silver impregnating solution contains silver in ionic form, generally in the form of a silver compound, complex, or salt, dissolved in a suitable aqueous solvent. The silver compound, complex, or salt should be water soluble and completely dissolved in the impregnation solution. Silver compounds useful for impregnation include, for example, silver oxalate, silver nitrate, silver oxide, silver carbonate, a silver carboxylate, silver citrate, silver phthalate, silver lactate, silver propionate, silver butyrate and higher fatty acid salts and combinations thereof. The concentration of silver in the solution is typically in the range from about 0.1% by weight to the maximum permitted by the solubility of the particular silver salt in the solubilizing agent employed. More typically, the concentration of silver is from about 0.5, 1, 2, 5, or 10 wt % to 15, 20, 25, 30, 35, 40, or 45 wt % by weight of the silver impregnating solution.

A wide variety of complexing or solubilizing agents may be employed to solubilize silver to the desired concentration in the impregnating medium. In particular embodiments, the complexing or solubilizing agent is ammonia or an organic amine. Generally, the organic amine possesses at least one primary or secondary amine group. The organic amine can be, for example, an alkylamine, alkylenediamine, dialkylenetriamine, or alkanolamine. Some examples of alkylamines include ethylamine, diethylamine, n-propylamine, di(n-propylamine), isopropylamine, diisopropylamine, n-butylamine, isobutylamine, sec-butylamine, and t-butylamine. Some examples of alkylenediamines include ethylenediamine (EDA), 1,2-propylenediamine, 1,3-propylenediamine, and 1,4-butylenediamine. Some examples of dialkylenetriamines include diethylenetriamine and dipropylenetriamine. Some examples of alkanolamines include ethanolamine, diethanolamine, propanolamine (i.e., 1-amino-2-propanol or 1-amino-3-propanol), and dipropanolamine. The organic amine is typically present in the impregnating solution in an amount from about 0.1 to about 5.0 moles per mole of silver, or about 0.2 to about 4.0 moles per mole of silver, or about 0.3 to about 3.0 moles per mole of silver. As used herein, the term "about" generally indicates no more than ±10%, ±5%, ±2%, or ±1% from a number. For example, the term "about 1 mole" generally indicates a value in the range of 0.9 to 1.1 moles in its broadest sense.

A polar organic additive (compound or molecule) containing two to four (i.e., two, three, or four) carbon atoms and two to four functional groups selected from hydroxy (OH), carboxylic acid (COOH), and amine ($NH_2$) groups is also included in the silver impregnating solution. The polar organic additive should be water soluble and completely dissolved in the impregnation solution. In the polar organic additive, a carboxylic acid group can only be present along with a hydroxy or amine group (or one, two, or more hydroxy and/or amine groups), and an amine group can only be present along with a hydroxy or carboxylic acid group (or one, two, or more hydroxy and/or carboxylic acid groups). The polar organic additive has a high boiling point, which herein refers to a boiling point of at least or above 100° C. The polar organic additive may have a boiling point of, for example, 100° C., 125° C., 150° C., 175° C., 200° C., 250° C., 300° C., 350° C., or 400° C., or a boiling within a range bounded by any two of the foregoing values, e.g., 100-400° C. or 150-400° C. In some embodiments, compounds having two or more hydroxy groups and more than four carbon atoms (e.g., 1,2-octanediol) are excluded from the silver impregnation solution. In other embodiments, compounds having three, four, or more than four hydroxy groups are excluded from the silver impregnation solution.

In a first set of embodiments, the polar organic additive contains two to four hydroxy groups. Some examples of polar organic additives containing two to four hydroxy groups include ethylene glycol, diethylene glycol, propylene glycol, glycerol, erythritol, and 1,1,2,2-ethanetetrol. In a second set of embodiments, the polar organic additive contains at least one hydroxy group and at least one carboxylic acid group. Some examples of polar organic additives containing at least one hydroxy group and at least one carboxylic acid groups include glycolic acid, 2-hydroxypropionic acid (lactic acid), 3-hydroxypropionic acid, 4-hydroxybutyric acid, and 3-hydroxybutyric acid. In a third set of embodiments, the polar organic additive contains at least one hydroxy group and at least one amine group. Some examples of polar organic additives containing at least one hydroxy group and at least one amine group include ethanolamine, diethanolamine, and triethanolamine. In a fourth set of embodiments, the polar organic additive contains at least one carboxylic acid group and at least one amine group. Some examples of polar organic additives containing at least one carboxylic acid group and at least one amine group include glycine, alanine, aspartic acid, 3-aminopropanoic acid (beta-alanine), 3-aminobutanoic acid, and 4-aminobutanoic acid. In some embodiments, any one or more generic or specific types of polar organic additives described above are excluded from the silver impregnation solution. The polar organic additive is typically present in an amount of at least 0.1 wt % by weight of the silver impregnating solution. In different embodiments, the polar organic additive is present in an amount of 0.1, 0.2, 0.5, 0.7, 1, 1.2, 1.5, 1.8, 2, 2.2, 2.5, 3, 3.5, 4, 4.5, or 5 wt %, or in an amount within a range bounded by any two of the foregoing values, e.g., 0.5-5 wt %, 1-5 wt %, 0.5-3 wt %, or 1-3 wt %.

The silver impregnation solution also includes water as a component. Since water is included, the silver impregnation solution is an aqueous solution. In some embodiments, water is included as the sole solvent (i.e., 100% of the solvent). In other embodiments, water is included along with one or more water-miscible solvents. Some examples of water-miscible solvents include water-soluble alcohols (e.g., methanol or ethanol), ketones (e.g., acetone), tetrahydrofuran, glymes (e.g., glyme, diglyme and tetraglyme), and the like, and their combinations. Generally, the water is present in an amount of at least 50, 60, 70, 80, or 90 wt % or vol % of a solvent mixture, but in some embodiments, water is present in a lesser amount, such as 40, 30, 20, or 10 wt % or vol %.

The silver impregnation solution may also include one or more catalyst promoting species (i.e., "promoting species" or "promoters"). The one or more promoting species can be any of those species, known in the art, that function to improve the activity or selectivity of the silver catalyst. The promoting species can be, for example, an alkali, alkaline earth, transition, or main group element. In particular embodiments, the promoting species is selected from one or more salts of lithium, cesium, rhenium, sulfur, tungsten, phosphorus, gallium, and fluorine. Some examples of salts of such elements include lithium nitrate, cesium hydroxide, ammonium sulfate, and ammonium rhenate. The promoting species, if present, should be completely soluble in the impregnation solution. In other embodiments, the impregnating solution does not include a promoting species.

In another aspect, the present disclosure is directed to a method for producing a catalyst effective in the oxidative conversion of ethylene to ethylene oxide by use of the above-described silver impregnation solution. In order to produce a catalyst for the oxidation of ethylene to ethylene oxide, a porous refractory carrier is first provided with a catalytically effective amount of silver on its surface. The catalytically effective amount of silver is provided by impregnating the carrier with the above-described silver impregnation solution. The carrier can be impregnated with the impregnation solution by any of the conventional methods known in the art, e.g., by excess solution impregnation (immersion), incipient wetness impregnation, spray coating, and the like. Typically, the carrier material is placed in contact with the impregnation solution until a sufficient amount of the solution is absorbed by the carrier, e.g., by immersing the refractory carrier into the silver impregnation solution. Preferably, the quantity of the impregnation solution used to impregnate the carrier is no more than is necessary to fill the pore volume of the carrier. Infusion of the impregnation solution into the carrier can be aided by application of a vacuum. A single impregnation or a series of impregnations, with or without intermediate drying, may be used, depending in part on the concentration of the silver in the solution. Impregnation procedures are described in, for example, U.S. Pat. Nos. 4,761,394, 4,766,105, 4,908,343, 5,057,481, 5,187,140, 5,102,848, 5,011,807, 5,099,041 and 5,407,888, all of which are incorporated herein by reference. Known procedures for pre-deposition, co-deposition, and post-deposition of the various promoters can also be employed.

After impregnation, the excess solution is preferably removed from the impregnated carrier, and the impregnated carrier is then subjected to a calcination process. The calcination process serves to reduce the ionic silver component to metallic silver and to remove volatile decomposition products from the silver-containing support. The calcination is typically accomplished by heating the impregnated carrier, typically at a gradual rate, to a temperature in a range of about 200° C. to about 600° C., more typically from about 200° C. to about 500° C., more typically from about 250° C. to about 500° C., and more typically from about 200° C. or 300° C. to about 450° C., at a reaction pressure in a range from about 0.5 to about 35 bar. In general, the higher the temperature, the shorter the required calcination period. A wide range of heating periods has been described in the art for the thermal treatment of impregnated supports. Reference is made to, for example, U.S. Pat. No. 3,563,914, which indicates heating for less than 300 seconds, and U.S. Pat. No. 3,702,259, which discloses heating from 2 to 8 hours at a temperature of from 100° C. to 375° C. to reduce the silver salt in the catalyst. A continuous or step-wise heating program may be used for this purpose. During calcination, the impregnated support is typically exposed to a gaseous atmosphere containing an inert gas, such as nitrogen. The inert gas may or may not also include a reducing agent. The amount of silver on the catalyst produced after calcination should be a catalytically effective amount of silver, which generally corresponds to an amount of silver of at least or above, for example, 10, 15, 18, 20, 25, or 30 wt % by weight of the carrier. In some embodiments, a lower temperature solvent removal (drying) step is employed before the calcination process. The solvent removal step typically employs a temperature of at least 80° C. or 100° C. and up to or less than 150° C. or 200° C. After the calcination process, the calcined catalyst is typically loaded into reactor tubes of an epoxidation reactor, typically a fixed bed tubular reactor, utilizing conventional loading methods well known to those skilled in the art. After loading, the catalyst bed may be swept by passing an inert gas such as nitrogen over the catalyst bed.

In some embodiments, the catalyst, as produced following calcination, is exposed to an atmosphere having a humidity level of at least or above 80%, 85%, or 90% for at least 6, 8, 10, 12, 15, 18, 20, 24, 36, or 48 hours. Moreover, it has herein been surprisingly found that exposure of the catalyst, produced as above, to high humidity over a period of time has a less deleterious effect on the selectivity and/or activity of the catalyst produced using a polar organic additive as described above compared to analogous catalysts prepared according to methods of the conventional art.

The catalyst carrier, which is typically porous, may be selected from any of the solid refractory carriers known in the art for use in silver-based catalysts. Some examples of carrier materials include alumina (e.g., alpha-alumina), charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics, and combinations thereof.

In some embodiments, the carrier includes or is completely composed of alumina, which may be a single type of alumina (e.g., alpha-alumina) or mixture of alumina compositions (e.g., gamma- and alpha-alumina). The alpha-alumina may be of a high purity, i.e., at least or greater than 95 wt % or 98 wt % alpha-alumina. The alpha-alumina carrier may or may not also include inorganic oxides other than alpha-alumina, such as silica, alkali metal oxides (e.g., sodium oxide) and trace amounts of other metal-containing or non-metal-containing additives or impurities.

The carrier precursor particles can be of any suitable size, and are typically microparticles. In different embodiments, the carrier microparticles can have a particle size (i.e., diameter, if substantially spherical) of precisely, about, at least, greater than, up to, or less than, for example, 1, 2, 3, 4, 5, 6, 7, 8, 9, 10, 12, 15, or 20 microns (µm), or the carrier microparticles may have a size within a range bounded by any two of the foregoing exemplary values. The carrier precursor particles may also be composed of two or more portions of microparticles of different sizes or size ranges, typically selected from the above exemplary sizes. Moreover, each portion of the carrier precursor particles may be in a suitable weight percentage by total weight of carrier precursor or finished carrier (before silver impregnation). In different embodiments, one or more portions of carrier microparticles in different size ranges may be present in an amount of precisely, about, at least, greater than, up to, or less than, for example, 1 wt %, 2 wt %, 5 wt %, 20 wt %, 25 wt %, 30 wt %, 40 wt %, 50 wt %, 60 wt %, 70 wt %, 80 wt %, 90 wt %, 95 wt %, 98 wt %, or 99 wt %, or within a weight percentage (wt %) range bounded by any of the foregoing values.

The carrier may be produced by conventional techniques well known to those skilled in the art, such as by combining alumina microparticles, a solvent (e.g., water), a temporary binder or burnout material, a permanent binder, and/or a porosity controlling agent, and then shaping, molding, or extruding the resulting paste, before firing (i.e., calcining) the preform by methods well known in the art. Temporary binders, or burnout materials, include cellulose, substituted celluloses, e.g., methylcellulose, ethylcellulose, and carboxyethylcellulose, stearates (such as organic stearate esters, e.g., methyl or ethyl stearate), waxes, granulated polyolefins (e.g., polyethylene and polypropylene), walnut shell flour, and the like, which are decomposable at the temperatures employed. The binders are responsible for imparting porosity to the carrier material. Burnout material is used primarily to ensure the preservation of a porous structure during the green (i.e., unfired phase) in which the mixture may be shaped into particles by molding or extrusion processes. Burnout materials are essentially completely removed during the firing to produce the finished carrier. Alternatively, the carrier may be purchased from a catalyst carrier provider. Some specific carrier formulations and methods for their preparation are described in U.S. Application Pub. No. 2007/0037991, the contents of which are herein incorporated by reference in their entirety.

The formed paste is extruded or molded into the desired shape and fired at a temperature typically from about 1200° C. to about 1600° C. to form the carrier. In embodiments in which the particles are formed by extrusion, it may be desirable to include conventional extrusion aids. Generally, the performance of the carrier is enhanced if it is treated by soaking the carrier in a solution of an alkali hydroxide, such as sodium hydroxide, potassium hydroxide, or an acid such as $HNO_3$ as described in U.S. Patent Application Publication No. 2006/0252643 A1. After treatment, the carrier is preferably washed, such as with water, to remove unreacted dissolved material and treating solution, and then optionally dried.

The carrier can be porous or non-porous, but is generally porous, typically with a B.E.T. surface area of at most 20 $m^2/g$. The B.E.T. surface area is more typically in the range of about 0.1 to 10 $m^2/g$, and more typically from 1 to 5 $m^2/g$. In other embodiments, the carrier is characterized by a B.E.T. surface area of about 0.3 $m^2/g$ to about 3 $m^2/g$, preferably about 0.6 $m^2/g$ to about 2.5 $m^2/g$, and more preferably about 0.7 $m^2/g$ to about 2.0 $m^2/g$. The B.E.T. surface area described herein can be measured by any suitable method, but is more preferably obtained by the method described in Brunauer, S., et al., *J. Am. Chem. Soc.*, 60, 309-16 (1938). The final carrier typically possesses a water absorption value (water pore volume) ranging from about 0.10 cc/g to about 0.80 cc/g, more typically from about 0.2 cc/g to about 0.8 cc/g, and more typically from about 0.25 cc/g to about 0.6 cc/g.

The carrier, if porous, can have any suitable distribution of pore diameters. As used herein, the term "pore diameter" is meant to indicate a pore size. The pore volume (and pore size distribution) described herein can be measured by any suitable method, such as by the conventional mercury porosimeter method described in, for example, Drake and Ritter, *Ind. Eng. Chem. Anal. Ed.*, 17, 787 (1945). Typically, the pore diameters are at least about 0.01 microns (0.01 µm), and more typically, at least about 0.1 µm. Typically, the pore diameters are no more than or less than about 10, 15, 20, 25, 30, 35, 40, 45, or 50 µm. In different embodiments, the pore diameters are about, at least, above, up to, or less than, for example, 0.2 µm, 0.5 µm, 1.0 µm, 1.2 µm, 1.5 µm, 1.8 µm, 2.0 µm, 2.5 µm, 3 µm, 3.5 µm, 4 µm, 4.5 µm, 5 µm, 5.5 µm, 6 µm, 6.5 µm, 7 µm, 7.5 µm, 8 µm, 8.5 µm, 9 µm, 9.5 µm, 10 µm, or 10.5 µm, or the pore diameters are within a range bounded by any two of the foregoing exemplary values. Any range of pore sizes, as particularly derived from any of the above exemplary values, may also contribute any suitable percentage of the total pore volume, such as at least, greater than, up to, or less than, for example, 1, 2, 5, 10, 15, 20, 25, 30, 40, 50, 60, 70, 80, 90, 95, or 98% of the total pore volume. In some embodiments, a range of pore sizes may provide the total (i.e., 100%) pore volume.

The carrier may possess a pore size distribution (e.g., within a range as set forth above) characterized by the presence of one or more pore sizes of peak concentration, i.e., one or more maxima (where the slope is approximately zero) in a pore size vs. pore volume distribution plot. A pore size of maximum concentration is also referred to herein as a peak pore size, peak pore volume, or peak pore concentration. Furthermore, each pore size distribution can be characterized by a single mean pore size (mean pore diameter) value. Accordingly, a mean pore size value given for a pore size distribution necessarily corresponds to a range of pore sizes that result in the indicated mean pore size value. Any of the exemplary pore sizes provided above can alternatively be understood to indicate a mean (i.e., average or weighted average) or median pore size in a pore size distribution. Any of the exemplary pore sizes provided above may also be interpreted to be the lower and upper bounds of a peak in a pore volume distribution plot.

In some embodiments, the carrier possesses a multimodal pore size distribution within any of the pore size ranges provided above. The multimodal pore size distribution can be, for example, bimodal, trimodal, or of a higher modality. The multimodal pore size distribution is characterized by the presence of different pore sizes of peak concentration (i.e., different peak pore sizes) in a pore size vs. pore volume distribution plot. The different peak pore sizes are preferably within the range of pore sizes given above. Each peak pore size can be considered to be within its own pore size distribution (mode), i.e., where the pore size concentration on each side of the distribution falls to approximately zero (in actuality or theoretically). In one embodiment, different pore size distributions, each having a peak pore size, are non-overlapping by being separated by a volume concentration of pores of approximately zero (i.e., at baseline). In another embodiment, different pore size distributions, each having a peak pore size, are overlapping by not being separated by a volume concentration of pores of approximately zero. Each mode of pores may contribute any suitable percentage of the total pore volume, such as any of the percentages or ranges thereof, provided above.

The macroscale shape and morphology of the carrier, i.e., after compounding and calcining of the carrier particles, can be any of the numerous shapes and morphologies known in the art. For example, the carrier can be in the form of particles, chunks, pellets, rings, spheres, three-holes, wagon wheels, cross-partitioned hollow cylinders, and the like, of a size preferably suitable for employment in fixed-bed epoxidation reactors. In particular embodiments, the macroscopic carrier units may have equivalent diameters of about, for example, 1, 2, 3, 4, 5, 6, 7, 8, 9, 10, 11, 12, 13, 14, or 15 mm, or an equivalent diameter within a range bounded by any two of the foregoing exemplary values. The equivalent diameter is preferably compatible with the internal diameter of the tubular reactors in which the catalyst is placed. As known in the art, the term "equivalent diameter" is used to express the size of an irregularly-shaped object by expressing the size of the object in terms of the diameter of a sphere having the same volume as the irregularly-shaped object. Alternatively, the equivalent diameter is the diameter of a sphere having the same external surface area (i.e., neglecting surface area within the pores of the particle) to volume ratio as the carrier units being employed.

The produced catalyst may also contain one or more promoting species. The one or more promoting species can be incorporated into the catalyst by, for example, being included in the silver impregnation solution, or by not being included in the impregnation solution and instead being incorporated in a separate step before or after the impregnation step, or both. As used herein, a "promoting amount"

of a certain component of a catalyst refers to an amount of that component that works effectively to provide an improvement in one or more of the catalytic properties of the catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement is exhibited in the activity rather than in the selectivity. All of the promoters, aside from the alkali metals, can be in any suitable form, including, for example, as zerovalent metals or higher valent metal ions.

In some embodiments, the produced catalyst may include a promoting amount of an alkali metal or a mixture of two or more alkali metals. Suitable alkali metal promoters include, for example, lithium, sodium, potassium, rubidium, cesium or combinations thereof. Cesium is often preferred, with combinations of cesium with other alkali metals also being preferred. The amount of alkali metal will typically range from about 10 ppm to about 3000 ppm, more typically from about 15 ppm to about 2000 ppm, more typically from about 20 ppm to about 1500 ppm, and even more typically from about 50 ppm to about 1000 ppm by weight of the total catalyst, expressed in terms of the alkali metal.

The produced catalyst may or may not also or alternatively include a promoting amount of a main group element or a mixture of two or more main group elements. Suitable main group elements include the elements in Group 3 (e.g., B, Al, or Ga), Group 4 (e.g., Si or Ge), Group 5 (e.g., P, As, or Sb), Group 6 (e.g., S), or Group 7 (e.g., F) of the Periodic Table of the Elements. For example, the carrier or catalyst can include a promoting amount of sulfur, phosphorus, boron, halogen (e.g., fluorine), or gallium, or a combination thereof. The main group element may be present in the form of a compound. Aside from the halogens, the main group element may be present in its elemental form.

The produced catalyst may or may not also or alternatively include a promoting amount of a transition metal or a mixture of two or more transition metals. Suitable transition metals include, for example, the elements in Group 3 (scandium group), Group 4 (titanium group), Group 5 (vanadium group), Group 6 (chromium group), Group 7 (manganese group), Groups 8-10 (iron, cobalt, nickel groups), Group 9 (copper group), and Group 10 (zinc group) of the Periodic Table of the Elements, as well as combinations thereof. More typically, the transition metal is an early transition metal, i.e., from Groups 3-6, such as, for example, hafnium, yttrium, molybdenum, tungsten, rhenium, chromium, titanium, zirconium, vanadium, tantalum, niobium, or a combination thereof. In one embodiment, the transition metal promoter is present in an amount from about 10 ppm to about 1000 ppm of total carrier or catalyst expressed as the metal. In another embodiment, the transition metal promoter is present in an amount from about 20 ppm to about 500 ppm of total carrier or catalyst expressed as the metal. In a further embodiment, the transition metal promoter is present in an amount from about 30 ppm to about 350 ppm of total carrier or catalyst expressed as the metal. Alternatively, the transition metal can be present in an amount of from about 0.1 micromoles per gram to about 10 micromoles per gram, more typically from about 0.2 micromoles per gram to about 5 micromoles per gram, and even more typically from about 0.5 micromoles per gram to about 4 micromoles per gram of the carrier or silver-containing catalyst, expressed in terms of the metal.

Of the transition metal promoters listed, rhenium (Re) is a particularly efficacious promoter for ethylene epoxidation high selectivity catalysts. The rhenium component in the carrier or catalyst can be in any suitable form, but is more typically one or more rhenium-containing compounds (e.g., a rhenium oxide) or complexes. The rhenium can be present in an amount of, for example, about 0.001 wt. % to about 1 wt. %. More typically, the rhenium is present in amounts of, for example, about 0.005 wt. % to about 0.5 wt. %, and even more typically, from about 0.01 wt. % to about 0.05 wt. % based on the weight of the total carrier, or by weight of the catalyst including the carrier, expressed as rhenium metal.

The produced catalyst may or may not also include a promoting amount of a rare earth metal or a mixture of two or more rare earth metals. The rare earth metals include any of the elements having an atomic number of 57-103. Some examples of these elements include lanthanum (La), cerium (Ce), and samarium (Sm). The amount of rare earth metal promoters can be used in amounts similar to those used for the transition metal promoters.

In a first set of embodiments, the carrier, before impregnation, contains one or more of any of the promoters described above. In a second set of embodiments, the carrier is provided with one or more promoters during silver impregnation with the silver-containing solution. In the latter embodiment, the carrier, before silver impregnation, may or may not contain any or all of the promoters described above. In a third set of embodiments, the carrier, after silver impregnation and calcination, is provided with one or more promoters in a post-processing step. In the latter embodiment, the carrier, before impregnation or calcination, may or may not contain any or all of the promoters described above.

In another aspect, the present disclosure is directed to a method for the vapor phase production of ethylene oxide by conversion of ethylene to ethylene oxide in the presence of oxygen by use of the catalyst described above. Generally, the ethylene oxide production process is conducted by continuously contacting an oxygen-containing gas with ethylene in the presence of the catalyst at a temperature in the range from about 180° C. to about 330° C., more typically from about 200° C. to about 325° C., and more typically from about 225° C. to about 270° C., at a pressure which may vary from about atmospheric pressure to about 30 atmospheres depending on the mass velocity and productivity desired. Pressures in the range of from about atmospheric to about 500 psi are generally employed. Higher pressures may, however, be employed within the scope of this disclosure. Residence times in large-scale reactors are generally on the order of about 0.1 to about 5 seconds. A typical process for the oxidation of ethylene to ethylene oxide comprises the vapor phase oxidation of ethylene with molecular oxygen in the presence of the inventive catalyst in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with catalyst.

The inventive catalysts are particularly active and selective in the conversion of ethylene to ethylene oxide. The conditions for conducting such an oxidation reaction in the presence of the catalyst herein described broadly comprise those described in the prior art. This applies, for example, to suitable temperatures, pressures, residence times, diluent materials (e.g., nitrogen, carbon dioxide, steam, argon, methane or other saturated hydrocarbons), the presence or absence of moderating agents to control the catalytic action (e.g., 1, 2-dichloroethane, vinyl chloride or ethyl chloride), the desirability of employing recycle operations or applying successive conversion in different reactors to increase the yields of ethylene oxide, and other particular conditions that may be beneficial for converting ethylene to ethylene oxide. Molecular oxygen employed as a reactant may be obtained from conventional sources, and may be relatively pure oxygen, or a concentrated oxygen stream comprising oxygen in a major amount with lesser amounts of one or more diluents such as nitrogen or argon, or air. In the production of ethylene oxide, reactant feed mixtures typically contain from about 0.5 to about 45% ethylene and from about 3 to about 15% oxygen, with the balance comprising comparatively inert materials including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or by-products, unreacted materials are typically returned to the oxidation reactor. For purposes of illustration only, the following are conditions that may be used in a conventional industrial ethylene oxide reactor unit: a gas hourly space velocity (GHSV) of 1500-10,000 h$^{-1}$, a reactor inlet pressure of 150-400 psig, a coolant temperature of 180-315° C., an oxygen conversion level of 10-60%, and an EO production (work rate) of 100-300 kg EO per cubic meters of catalyst per hour. Typically, the feed composition at the reactor inlet comprises 1-40% ethylene, 3-12% oxygen, 0.3-40% $CO_2$, 0-3% ethane, 0.3-20 ppmv total concentration of organic chloride moderator, with the balance of the feed being argon, methane, nitrogen, or mixtures thereof.

The produced catalyst preferably exhibits a selectivity of at least 85% for the conversion of ethylene to ethylene oxide. In different embodiments, the produced catalyst exhibits a selectivity of about or at least, for example, 85%, 86%, 87%, 88%, 89%, 90%, 91%, 92%, or 93%, or a selectivity within a range bounded by any two of the foregoing values, particularly for the start-up (i.e., "initiation" or "activation") phase of the process. The start-up phase of the ethylene conversion process generally refers to the initial 150, 125, or 100 hours of operation of the catalyst under specific conditions, which may be any of the conditions described above or any of the specific start-up conditions known in the art designed to prime or ready the catalyst for ethylene oxide production. The type of start-up process that can be used in the present invention is not limited to any specific type. For further details on some typical conditions employed in a start-up process, reference is made to, for example, U.S. Pat. No. 8,883,675, the contents of which are herein incorporated by reference.

In other embodiments, the process of ethylene oxide production includes the addition of oxidizing gases to the feed to increase the efficiency of the process. For example, U.S. Pat. No. 5,112,795 discloses the addition of 5 ppm of nitric oxide to a gas feed having the following general composition: 8 volume % oxygen, 30 volume % ethylene, about 5 ppmw ethyl chloride, with the balance as nitrogen.

Some examples of organic chloride moderators that can be employed in the present disclosure include, for example, organic halides, such as $C_1$ to $C_8$ halohydrocarbons, which, may be, for example, methyl chloride, ethyl chloride, ethylene dichloride, vinyl chloride, or a mixture thereof. Also suitable are hydrogen-free chlorine sources, such as perhalogenated hydrocarbons and diatomic chlorine, both of which are particularly effective as moderators in gas phase epoxidation. Perhalogenated hydrocarbons refer to organic molecules in which all of the hydrogen atoms in a hydrocarbon have been substituted with halogen atoms. Some examples of perhalogenated hydrocarbons include trichlorofluoromethane and perchloroethylene. The concentration of the moderator should be controlled so as to balance a number of competing performance characteristics. For example, moderator concentration levels that result in improved activity may simultaneously lower selectivity. Controlling moderator concentration level is particularly important with rhenium-containing catalysts of the present disclosure, because as the rhenium-containing catalysts age, the moderator concentration must be carefully monitored so as to continually increase, within small increments, since optimal selectivity values are obtained only within a narrow moderator concentration range.

The resulting ethylene oxide is separated and recovered from the reaction products using methods known in the art. The ethylene oxide process may include a gas recycle process wherein a portion or substantially all of the reactor effluent is readmitted to the reactor inlet after substantially removing the ethylene oxide product and byproducts. In the recycle mode, carbon dioxide concentrations in the gas inlet to the reactor may be, for example, about 0.3 to about 6 volume percent, and more typically, about 0.3 to about 2.0 volume percent.

Examples have been set forth below for the purpose of further illustrating the invention. The scope of this invention is not to be in any way limited by the examples set forth herein.

EXAMPLES

Brief Summary of Results

It has herein been discovered that including certain organic compounds (polar organic additives) at a level of 0.5-3% to the silver impregnation solution prior to carrier impregnation results in a catalyst with superior start-up performance. Such positive behavior was observed, in particular, for ethylene glycol, glycerol, glycolic acid and glycine. The improvement in the start-up selectivity was even more significant for catalysts that were stored in humid (90%+) air after preparation. Scanning electron microscope (SEM) analysis suggested better promoter dispersion when the organic additives were included. At the same time, 1,2-octanediol, oleic acid, gluconic acid and citric acid as additives produced catalysts with inferior activity and/or selectivity. Based on these results, it is speculated that, in general, polar organic additives with a medium to high boiling point, in particular those with 2-4 carbon atoms and 2-6 heteroatoms in the structure and a boiling point in the range of 150-400° C., are particularly suitable for this invention.

Experimental Details and Results

A small amount (1-3%) of high-boiling liquid was added to the promoted silver solution, but otherwise the catalyst was impregnated as usual and calcined in the nitrogen BTU at 400° C. as usual. In case of glycerol, although some of it may still have been present in the catalyst after the calcination, thermogravimetric analysis (TGA) suggested the remainder amount, approx. 0.07% wt in catalyst, was 10% or less of the originally impregnated.

Figure 1B:
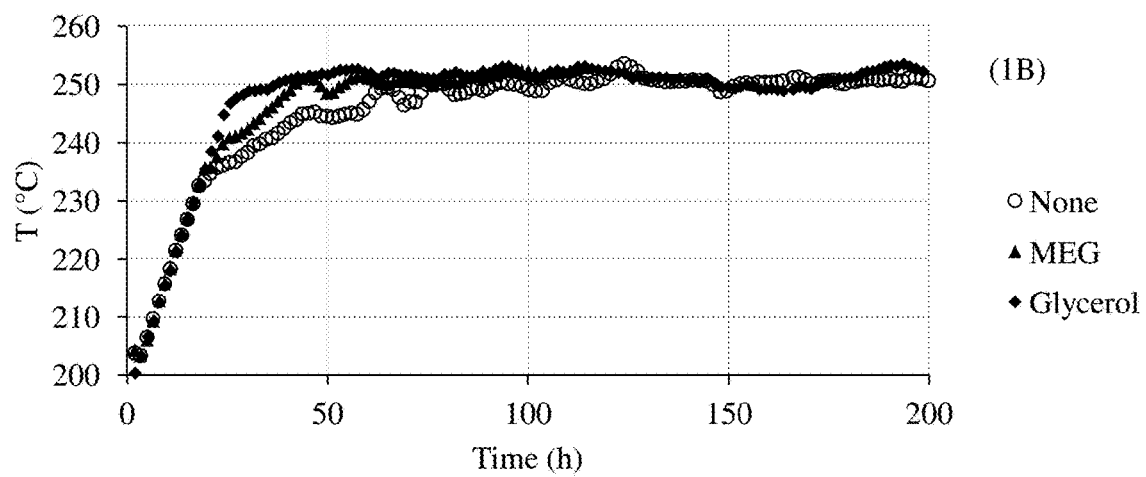

FIGS. 1A and 1B are graphs showing the microreactor test results (selectivity and activity, respectively) for SynDox™-400 commercial catalyst and the catalyst prepared from same solution which was modified with 2% ethylene glycol (MEG)- or glycerol-modified formulations. Feed: $C_2H_4/O_2/CO_2$ 30/7/1, $\Delta EO$=3.8%. FIG. 1A shows selectivity results vs. time, while FIG. 1B shows temperature (T) results vs. time. Catalysts were tested under the above conditions. Ethylene chloride in the feed was initially set to 1 ppm, and was not increased until the temperature reached 245° C. The catalyst produced with glycerol as additive (2%, b.p. 290° C.) was most selective, reaching 88% selectivity at approximately 13 hours on feed and 223° C. When ethylene glycol (2%, b.p. 197° C.) was used as additive, this selectivity was reached at approx. 56 hours and 250° C. The catalyst without high-boiling additive (water added to compensate) was found to be the most active and reached target $\Delta EO$ of 3.8 at 236° C., however, the selectivity was only 85-86%. The temperature continued to rise due to low chloride gaseous promoter, but this self-conditioning took 97 hours to reach 88% selectivity and 140 hours to reach 89.5% peak selectivity with 2.2 ppm ethyl chloride. The temperature and selectivity curves of all three catalysts eventually merge, indicating the same performance after 100-150 hours conditioning period, but the addition of MEG and especially glycerol clearly show more efficient start-ups of the catalyst.

Figure 2A:
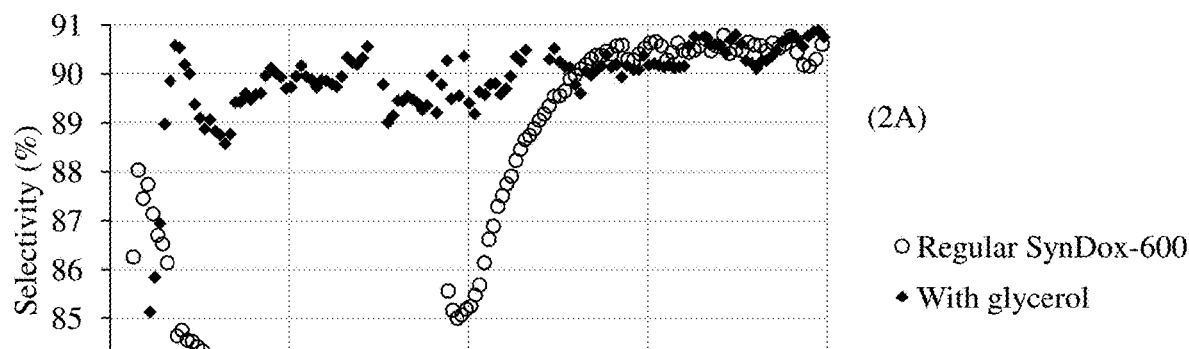
FIGS. 2A and 2B are graphs showing results of microreactor demo testing of SynDox™-600 commercial catalyst and the catalyst modified with 2% glycerol-modified formulation.
Figure 2B:
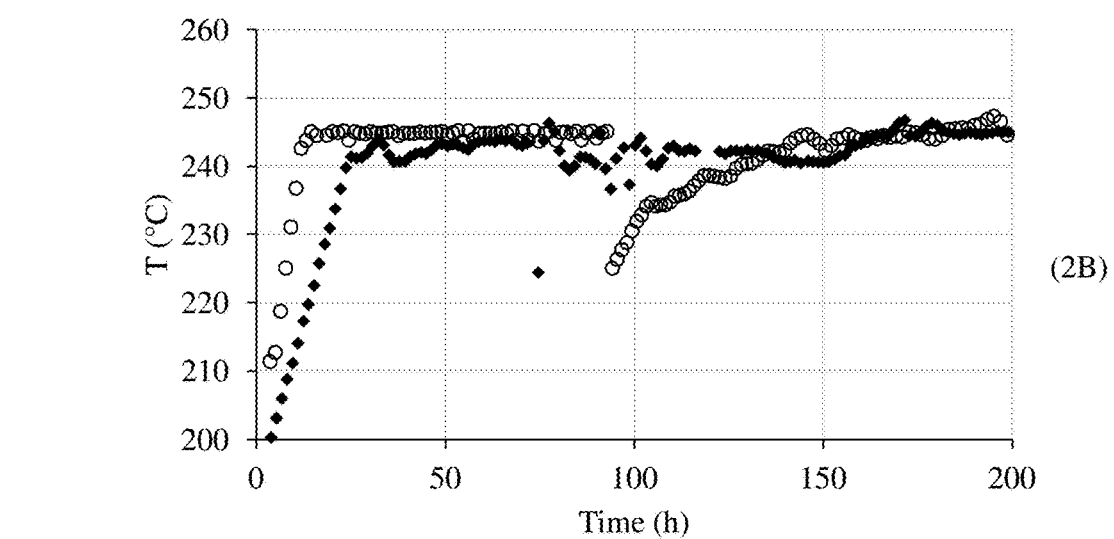

SynDox™-600 commercial catalysts were tested as well. FIGS. 2A and 2B are graphs showing results of microreactor testing of SynDox™-600 commercial catalyst and the catalyst modified with 2% glycerol-modified formulation. Feed: $C_2H_4/O_2/CO_2$ 30/7/1, $\Delta EO$=3.8% (regular catalyst was conditioned in 8/4/4 feed for 3 days at 245° C.). FIG. 2A shows selectivity results vs. time, while FIG. 2B shows temperature (T) results vs. time. In this case, catalysts with 1, 2 and 3% of glycerol in the promoting solution demonstrated similar performance, but had a clearly advantageous start-up even when the regular catalyst was conditioned as demonstrated in FIGS. 2A and 2B.

Figures 3A, 3B, 3C:
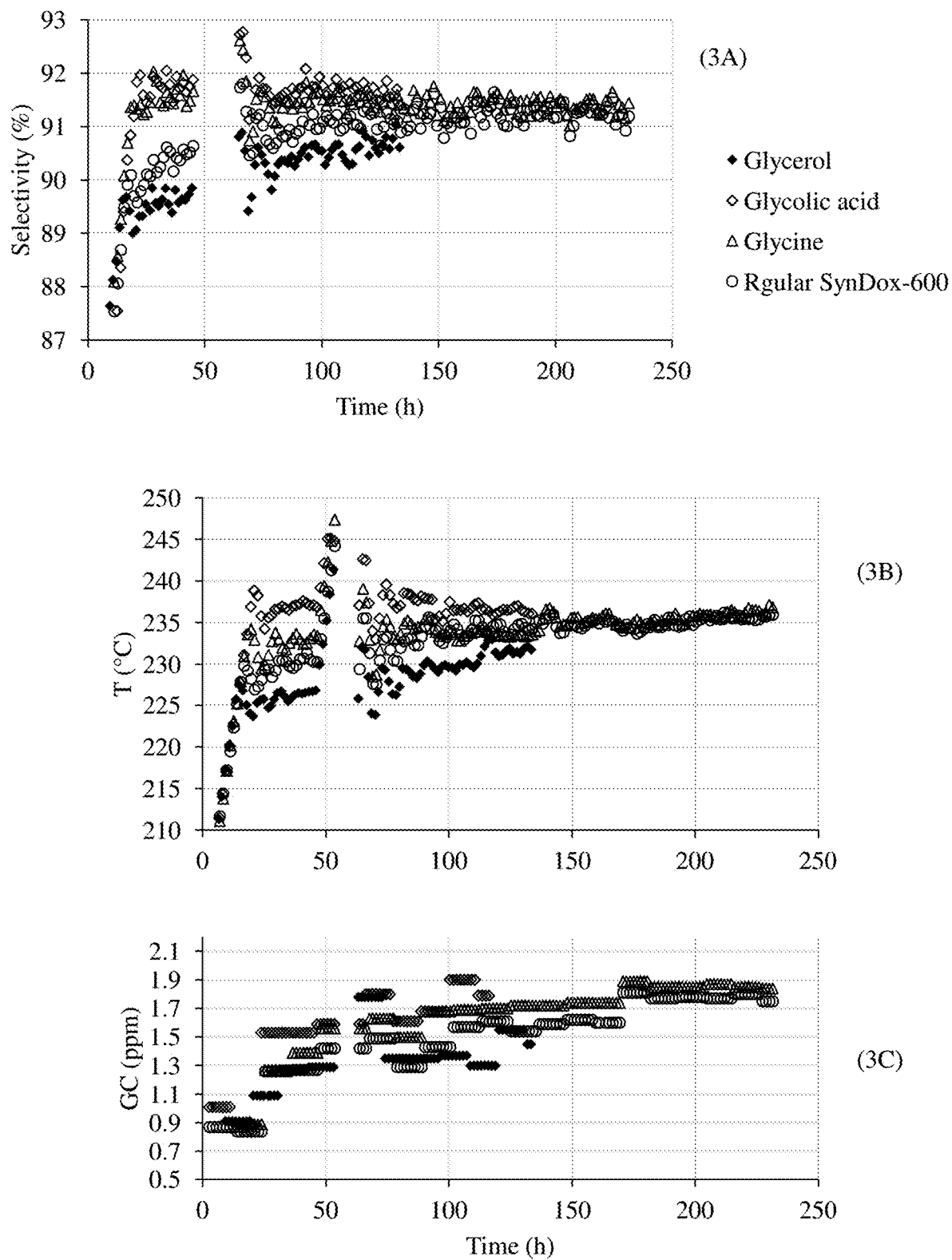
FIGS. 3A, 3B and 3C are graphs showing effects of additives on start-up performance of SynDox™-600 commercial catalyst, with or without the indicated additives, directly after preparation (9 g catalyst charge, feed $C_2H_4/O_2/CO_2$ 30/7/1, $\Delta EO=2.5\%$).
Figures 4A, 4B, 4C:
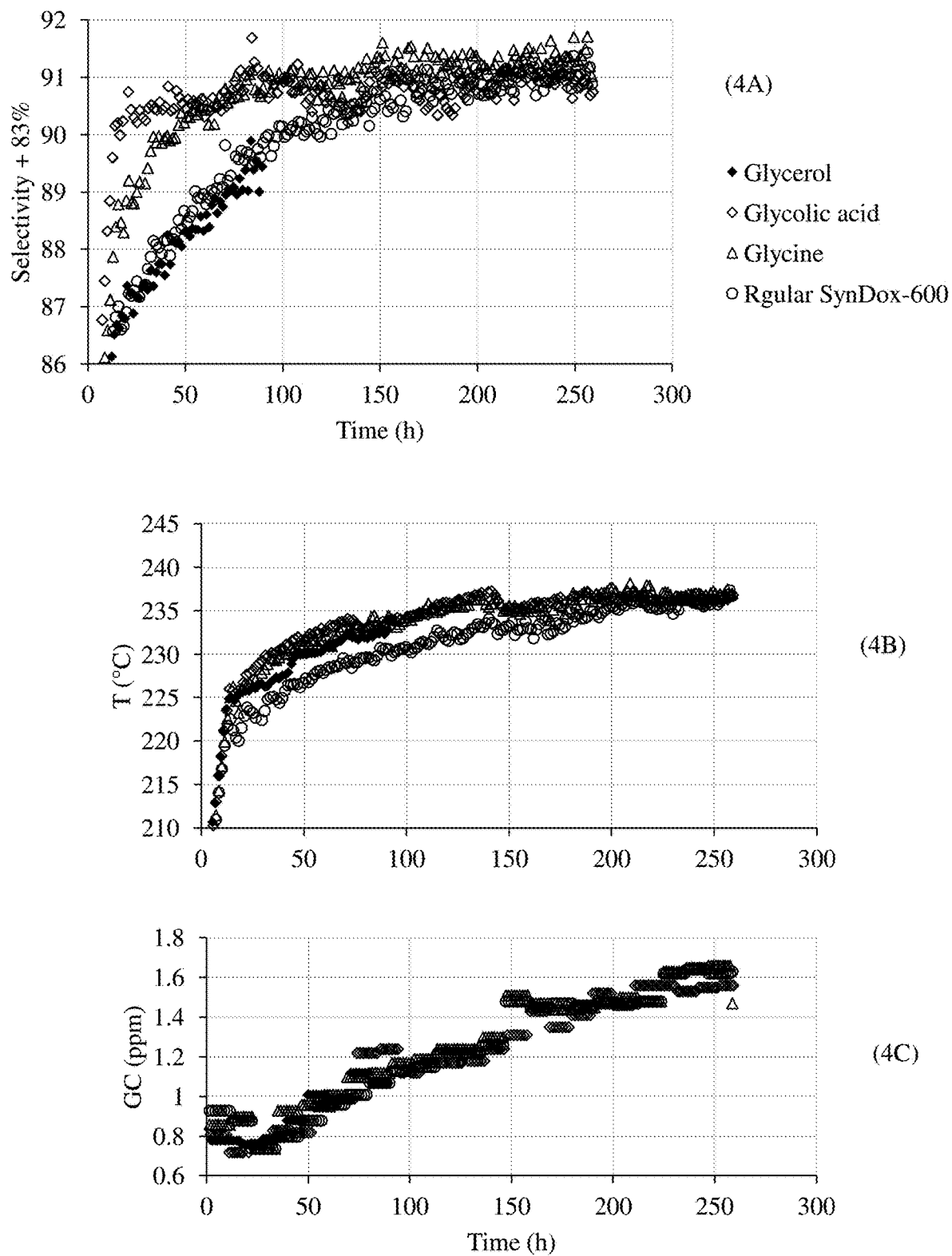
FIGS. 4A, 4B and 4C are graphs showing effects of additives on start-up performance of SynDox™-600 commercial catalyst, with or without the indicated additives, after 10-day storage in 90%+ humidity (9 g catalyst charge, feed $C_2H_4/O_2/CO_2$ 30/7/1, $\Delta EO=2.5\%$).

Four catalysts were prepared side by side: commercial SynDox™-600, and the rest were prepared by doping the same solution with 0.5% of an additive. Three additives tested were glycerol, glycolic acid and glycine. The Cs loading was targeted on a low side in these catalysts, as catalysts with lower Cs generally require more time to develop. The four catalysts were then tested twice, once directly after the preparation (with selectivity, activity, and GC results shown in FIGS. 3A, 3B, and 3C, respectively), and the second time after their storage for 10 days at 90+% humidity in enclosed containers with water (with selectivity, activity, and GC results shown in FIGS. 4A, 4B, and 4C, respectively). FIG. 3A shows the results for selectivity results vs. time, while FIG. 3B shows the temperature (T) vs. time results and FIG. 3C shows the GC (ppm) vs. time results. Similarly, FIG. 4A shows the results for selectivity vs. time, while FIG. 4B shows the temperature (T) vs. time results and FIG. 4C shows ethyl chloride by GC (ppm) vs. time results.

Figure 5A:
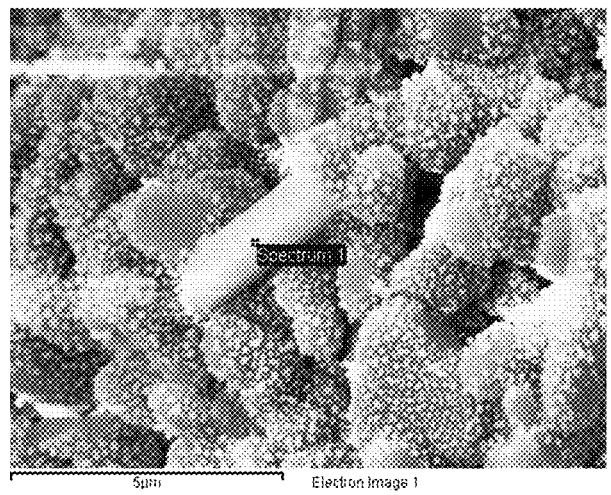
FIGS. 5A, 5B, 5C, and 5D show two different scanning electron micrograph (SEM) images (FIGS. 5A and 5C) and corresponding energy-dispersive X-ray spectroscopy (EDS) scans (FIGS. 5B and 5D) of SynDox™-600 commercial catalyst, after being stored in 90+% humidity for 10 days.
Figure 5B:
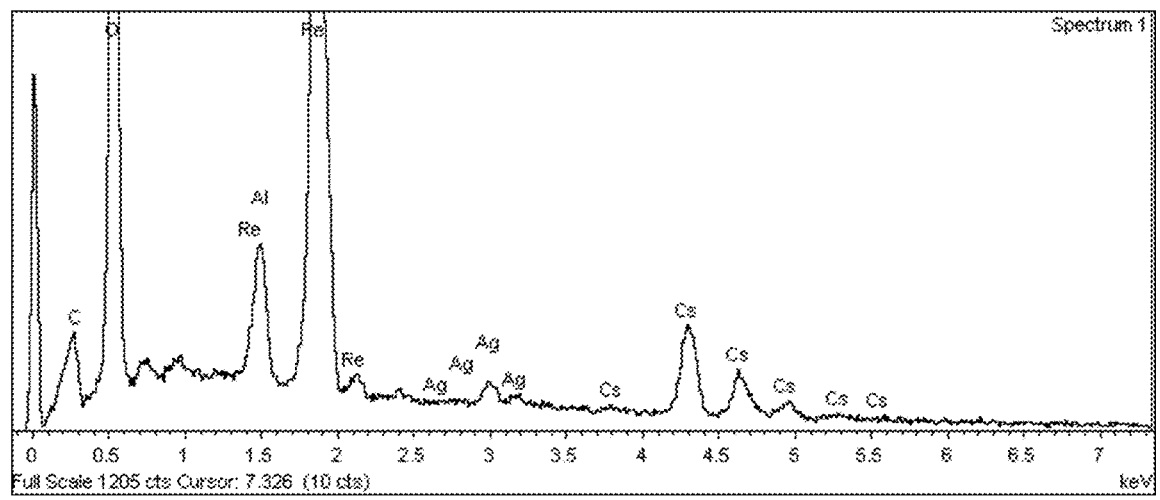
Figure 5C:
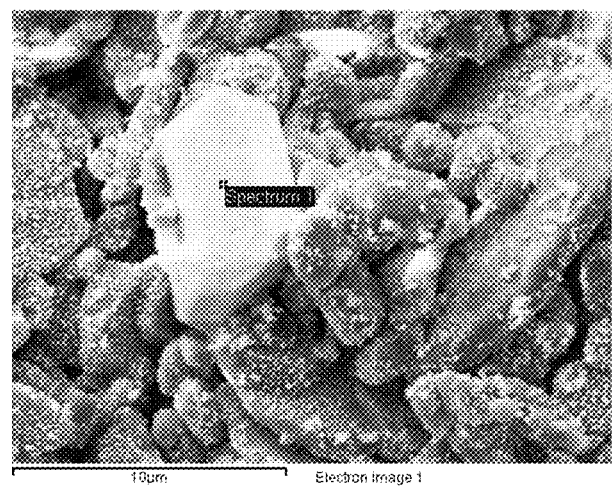
Figure 5D:
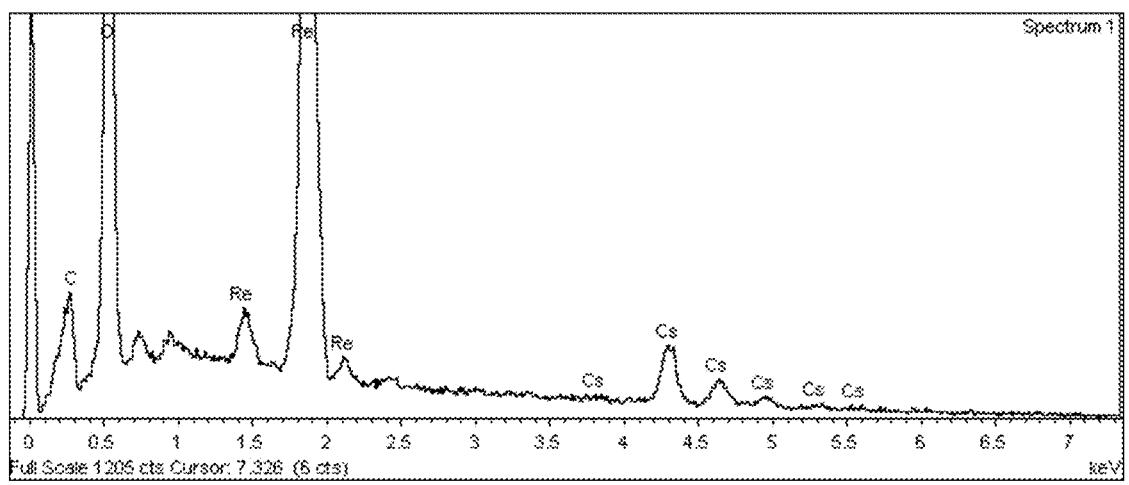
Figure 5E:
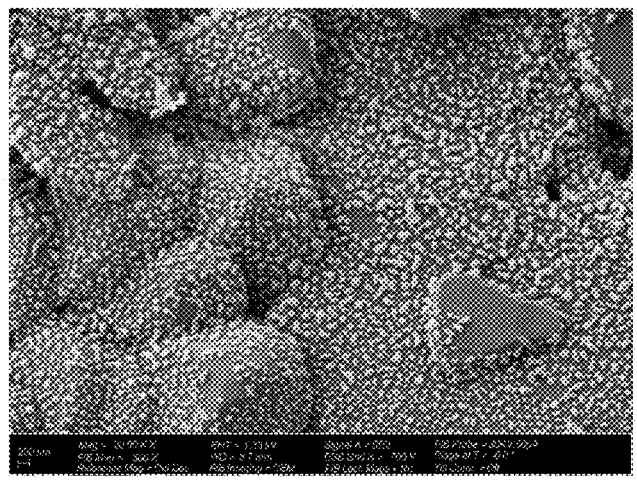
FIG. 5E shows a scanning electron micrograph (SEM) image of the catalyst prepared with glycine as a polar additive in the silver impregnation formulation, after being stored in 90+% humidity for 10 days.

The following mild industrial-simulating testing conditions were used: 9 g catalyst, $C_2H_4/O_2/CO_2$ 30/7/1 feed, $\Delta EO$=2.5%. Glycerol as additive did not show any benefit. It appears that at least 1% of glycerol in the formulation is preferable to achieve an enhanced start-up. On the other hand, both glycine and glycolic acid provided an instant selectivity start-up, in both immediately prepared and humidified catalyst, and the effect surprisingly increased for the stored catalysts. FIGS. 5A and 5C show two different scanning electron micrograph (SEM) images of SynDox™-600 commercial catalyst, after being stored in 90+% humidity for 10 days. The corresponding energy-dispersive X-ray spectroscopy (EDS) scans are provided in FIGS. 5B and 5D, respectively. Notably, the "spectrum 1" labels in the SEM images indicate formations that were investigated with corresponding EDS scans for elemental composition, and were found to be enriched with Cs and Re promoters. No unusual formations were observed after humidity treatment of the catalysts prepared using high-boiling polar organic additives as shown, for example, in FIG. 5E for the catalyst prepared with glycine. Without being bound by theory, the observed effect of the additives is most likely due to a more efficient promoter redistribution during the calcination process, either through simple dissolution or by creation of additional ionic species, e.g., carboxylates that enhance Cs dispersion.

While there have been shown and described what are presently believed to be the preferred embodiments of the present disclosure, those skilled in the art will realize that other and further embodiments can be made without departing from the spirit and scope of the present disclosure, and this disclosure includes all such modifications that are within the intended scope of the claims set forth herein.

What is claimed is:

1. A silver impregnation solution comprising:
   (i) silver ions,
   (ii) a polar organic additive containing two to four carbon atoms and at least one hydroxy group and at least one carboxylic acid group; and
   (iii) water;
   wherein components (i) and (ii) are water soluble and dissolved in said impregnation solution;
   wherein said polar organic additive is present in said silver impregnation solution in an amount of 0.1-5 wt %; and wherein the silver impregnation solution excludes a main group promoting species.

2. The silver impregnation solution of claim 1, wherein said polar organic additive has a boiling point of 100-400° C.

3. The silver impregnation solution of claim 1, wherein said polar organic additive has a boiling point of 150-400° C.

4. The silver impregnation solution of claim 1, wherein said polar organic additive is present in said silver impregnation solution in an amount of 1-5 wt %.

5. The silver impregnation solution of claim 1, wherein said polar organic additive is present in said silver impregnation solution in an amount of 0.5-3 wt %.

6. The silver impregnation solution of claim 1, wherein said polar organic additive is present in said silver impregnation solution in an amount of 1-3 wt %.

7. The silver impregnation solution of claim 1, wherein said polar organic additive is selected from glycolic acid, lactic acid, 3-hydroxypropionic acid, 4-hydroxybutyric acid, and 3-hydroxybutyric acid.

8. The silver impregnation solution of claim 1, wherein said silver impregnation solution further comprises (iv) at least one organic amine.

9. The silver impregnation solution of claim 8, wherein said organic amine is ethylene diamine.

10. The silver impregnation solution of claim 1, wherein said silver impregnation solution further comprises a catalyst promoting species selected from alkali, alkaline earth, and transition metals.

11. The silver impregnation solution of claim 1, wherein said silver impregnation solution further comprises rhenium as a catalyst promoting species.

12. The silver impregnation solution of claim 1, wherein said silver impregnation solution further comprises cesium as a catalyst promoting species.

13. The silver impregnation solution of claim 1, wherein said polar organic additive contains two to four carbon atoms, one hydroxy group, and one carboxylic acid group.

14. The silver impregnation solution of claim 1, wherein said polar organic additive is glycolic acid.

15. The silver impregnation solution of claim 1, wherein said polar organic additive is present in said silver impregnation solution in an amount of 0.1-1.8 wt %.

16. The silver impregnation solution of claim 1, wherein said polar organic additive is present in said silver impregnation solution in an amount of 0.1-1.5 wt %.

17. A silver impregnation solution consisting of:
(i) silver ions,
(ii) a polar organic additive containing two to four carbon atoms and at least one hydroxy group and at least one carboxylic acid group;
(iii) water;
(iv) optionally, at least one organic amine; and
(v) optionally, a promoting species;
wherein components (i) and (ii) are water soluble and dissolved in said impregnation solution;
wherein said polar organic additive is present in said silver impregnation solution in an amount of 0.1-5 wt %.

18. A method for producing a catalyst effective in the oxidative conversion of ethylene to ethylene oxide, the method comprising subjecting a refractory carrier impregnated with a silver impregnation solution to a calcination process, wherein said silver impregnation solution comprises:
(i) silver ions,
(ii) a polar organic additive containing two to four carbon atoms and at least one hydroxy group and at least one carboxylic acid group;
and
(iii) water;
wherein components (i) and (ii) are water soluble and dissolved in said impregnation solution;
and wherein said polar organic additive is present in said silver impregnation solution in an amount of 0.1-5 wt %; and wherein the silver impregnation solution excludes a main group promoting species.

19. The method of claim 18, wherein the refractory carrier comprises alumina.

20. The method of claim 18, wherein the refractory carrier is impregnated with the silver impregnation solution by immersing the refractory carrier into the silver impregnation solution.

21. The method of claim 18, wherein said polar organic additive has a boiling point of 100-400° C.

22. The method of claim 18, wherein said polar organic additive has a boiling point of 150-400° C.

23. The method of claim 18, wherein said polar organic additive is present in said silver impregnation solution in an amount of 1-5 wt %.

24. The method of claim 18, wherein said polar organic additive is present in said silver impregnation solution in an amount of 0.5-3 wt %.

25. The method of claim 18, wherein said polar organic additive is present in said silver impregnation solution in an amount of 1-3 wt %.

26. The method of claim 18, wherein said polar organic additive is selected from glycolic acid, lactic acid, 3-hydroxypropionic acid, 4-hydroxybutyric acid, and 3-hydroxybutyric acid.

27. The method of claim 18, wherein said silver impregnation solution further comprises (iv) at least one organic amine.

28. The method of claim 27, wherein said organic amine is ethylene diamine.

29. The method of claim 18, wherein said silver impregnation solution further comprises a catalyst promoting species selected from alkali, alkaline earth, and transition metals.

30. The method of claim 18, wherein said silver impregnation solution further comprises rhenium as a catalyst promoting species.

31. The method of claim 18, wherein said silver impregnation solution further comprises cesium as a catalyst promoting species.

32. The method of claim 18, wherein said catalyst, as produced after said calcination process, is exposed to an atmosphere having a humidity level of at least 80% for at least six hours.

33. The method of claim 18, wherein said catalyst, as produced after said calcination process, is exposed to an atmosphere having a humidity level of at least 90% for at least six hours.

* * * * *